(12) United States Patent
Boulnois et al.

(10) Patent No.: US 9,211,125 B2
(45) Date of Patent: Dec. 15, 2015

(54) FLEXIBLE CLIP APPLIER

(75) Inventors: Jean-Luc Boulnois, Boston, MA (US);
Tomohiro Kawano, Tokyo (JP);
Masayasu Sato, Saitama-ken (JP)

(73) Assignee: MICROLINE SURGICAL, INC., Beverly, MA (US)

( * ) Notice: Subject to any disclaimer, the term of this patent is extended or adjusted under 35 U.S.C. 154(b) by 673 days.

(21) Appl. No.: 12/256,698

(22) Filed: Oct. 23, 2008

(65) Prior Publication Data
US 2010/0106167 A1   Apr. 29, 2010

(51) Int. Cl.
| | |
|---|---|
| A61B 17/10 | (2006.01) |
| A61B 17/128 | (2006.01) |
| A61B 17/00 | (2006.01) |
| A61B 17/122 | (2006.01) |
| A61B 17/29 | (2006.01) |

(52) U.S. Cl.
CPC ....... *A61B 17/1285* (2013.01); *A61B 17/00234* (2013.01); *A61B 17/1227* (2013.01); *A61B 2017/00292* (2013.01); *A61B 2017/2905* (2013.01)

(58) Field of Classification Search
CPC ............. A61B 17/1227; A61B 17/128; A61B 2017/00292
USPC ............... 606/139, 142, 143, 157; 227/175.1, 227/175.3; 600/139, 141, 142
See application file for complete search history.

(56) References Cited

U.S. PATENT DOCUMENTS

| | | | |
|---|---|---|---|
| 4,658,822 A | 4/1987 | Kees, Jr. | |
| 4,966,603 A | 10/1990 | Focelle et al. | |
| 5,042,707 A * | 8/1991 | Taheri | 606/213 |
| 5,156,609 A * | 10/1992 | Nakao et al. | 606/142 |
| 5,382,255 A | 1/1995 | Castro et al. | |
| 5,593,414 A | 1/1997 | Shipp et al. | |
| 5,858,018 A | 1/1999 | Shipp et al. | |
| 5,904,693 A | 5/1999 | Dicesare et al. | |
| 5,993,465 A | 11/1999 | Shipp et al. | |
| 6,139,555 A * | 10/2000 | Hart et al. | 606/139 |
| 6,290,575 B1 | 9/2001 | Shipp | |
| 6,350,269 B1 | 2/2002 | Shipp et al. | |
| 6,607,540 B1 | 8/2003 | Shipp | |
| 6,652,539 B2 | 11/2003 | Shipp et al. | |

(Continued)

FOREIGN PATENT DOCUMENTS

| | | |
|---|---|---|
| EP | 1757236 | 2/2007 |
| JP | 63-45747 | 3/1988 |

(Continued)

OTHER PUBLICATIONS

Search report from E.P.O., mail date is Aug. 6, 2012.

(Continued)

*Primary Examiner* — Gregory Anderson
*Assistant Examiner* — Christina Lauer
(74) *Attorney, Agent, or Firm* — Greenblum & Bernstein, P.L.C.

(57) ABSTRACT

A clip applier includes a shaft having a proximal end and a distal end. Further, the distal end of the shaft includes a flexible tool having at least two rails connected to each other by at least one jointed connection, and the at least two rails configured to rotate about the jointed connection. Additionally, a pair of jaws may be provided at a distal end of the flexible tool. Further, an actuator may be provided at the proximal end of the shaft to advance the surgical clip within the flexible tool.

17 Claims, 10 Drawing Sheets

FIG. 5A

(56) References Cited

U.S. PATENT DOCUMENTS

| | | | |
|---|---|---|---|
| 6,652,545 B2 | 11/2003 | Shipp et al. | |
| 7,914,543 B2 * | 3/2011 | Roth et al. | 606/153 |
| 2002/0068945 A1 * | 6/2002 | Sixto et al. | 606/142 |
| 2002/0082615 A1 | 6/2002 | Shipp et al. | |
| 2002/0082618 A1 | 6/2002 | Shipp et al. | |
| 2004/0097972 A1 | 5/2004 | Shipp et al. | |
| 2004/0106936 A1 | 6/2004 | Shipp et al. | |
| 2005/0119677 A1 | 6/2005 | Ship | |
| 2005/0149063 A1 | 7/2005 | Young et al. | |
| 2006/0094932 A1 | 5/2006 | Goldfarb et al. | |
| 2006/0094933 A1 * | 5/2006 | Goldfarb et al. | 600/229 |
| 2007/0049950 A1 | 3/2007 | Theroux et al. | |
| 2007/0093856 A1 | 4/2007 | Whitfield et al. | |
| 2007/0282355 A1 | 12/2007 | Brown et al. | |
| 2008/0114377 A1 | 5/2008 | Shibata et al. | |
| 2008/0306492 A1 | 12/2008 | Shibata et al. | |

FOREIGN PATENT DOCUMENTS

| | | |
|---|---|---|
| JP | 10-510169 | 10/1998 |
| JP | 2008-086778 | 4/2008 |
| JP | 2008-302045 | 12/2008 |
| WO | 96/10957 | 4/1996 |
| WO | 2005/011745 | 2/2005 |
| WO | 2007/142977 | 12/2007 |
| WO | 2008/045350 | 4/2008 |
| WO | 2008/045374 | 4/2008 |

OTHER PUBLICATIONS

Japan Office action, mail date is Mar. 21, 2012.
Canadian Official Action, mail date is Jan. 17, 2013.
Japan Office action, dated Jan. 28, 2014 along with an english translation thereof.

* cited by examiner

FLEXIBLE CLIP APPLIER

BACKGROUND OF THE INVENTION

I. Field of the Invention

The present invention relates generally to a flexible clip applier for applying a surgical clip.

II. Discussion of the Background Art

Surgical instruments have been developed for use with a variety of endoscopic surgical techniques and procedures. In particular, in the conventional art, clip applier for occlusion and ligation of vessels are well known.

Conventional clip appliers typically include an elongated body having a proximal end connected to an actuating mechanism, and a pair of jaws supported at the distal end.

In one exemplary embodiment of a conventional art clip applier, the jaws include a pair of opposing jaw members which are movable with respect to each other. In this regard, the jaws may be configured to grasp a target area (e.g., a section of body tissue) therebetween. Thus, the jaws are moved relative to each other when an operator operates an actuating handle coupled to an actuating mechanism. In some conventional art clip appliers, multiple surgical clips are supported in the elongated body and moved distally, one at a time, into the jaw members in preparation for being applied to a section of tissue.

There are several disadvantages associated with conventional clip appliers as described and as currently used. For example, conventional clip appliers have a rigid elongated body for receiving surgical clips therein. Therefore, these conventional clip appliers cannot extend through, e.g., an endoscope having an elongated channel that includes at least one curved portion.

Additionally, because of the rigid elongated body of the conventional clip applier, the distal end of the clip applier (e.g., proximate the jaws) may become damaged during assembly, transport, etc.

SUMMARY OF THE INVENTION

Accordingly, what is needed is a clip applier which can be used in a variety of endoscopic procedures including in an endoscope having a elongated channel that includes at least one curved portion. Further, what is also needed is a durable, resilient clip applier which is resistant to damage that may occur to conventional prior art clip appliers having a rigid elongated body and distal end.

These and other features of the present disclosure will be apparent from review of the specification and accompanying drawings.

Accordingly, a non-limiting embodiment of the present invention provides a clip applier for applying a surgical clip to a target area during a surgical procedure. In this regard, the clip applier includes a shaft having a proximal end and a distal end. Further, the distal end of the shaft includes a flexible tool having at least two rails connected to each other by at least one jointed connection. Additionally, the at least two rails are configured to rotate about the jointed connection, and a pair of jaws may be provided at a distal end of the flexible tool. Further, an actuator may be provided at the proximal end of the shaft to advance the surgical clip within the flexible tool.

Additional, the at least two rails may include at least three rails, and the at least one jointed connection may include a plurality of jointed connections such that a jointed connection of the plurality of jointed connections connects the at least two rails of the at least three rails. In this regard, the jointed connection may include a pin or any other suitable connector which allows relative rotation between the rails. Additionally, the at least two rails and the jointed connection may be configured together to allow the distal end of the shaft to bend at a plurality of locations.

Further, in accordance with an additional feature, the actuator may include a hand piece. Additionally, the actuator may include a flexible (e.g., deformable) wire connected to a pusher and coupled to the hand-piece. In this regard, both the flexible wire and pusher may be actuatable towards the distal end of the shaft such that, upon actuation of the handpiece, the pusher may engage a rear surface of a proximal-most surgical clip so as to advance the surgical clip within the flexible tool and towards the jaws.

Additionally, a length of the surgical clip may be approximately the same as a length of the rails.

In another feature of the present inventions, the jaws may be provided with an inwardly projecting ledge. In this regard, the ledge may be configured to engage the surgical clip and temporarily expand the surgical clip from a pre-biased closed position to an open position so as to engage (or clamp) a target area.

Additionally, the shaft may include an outer pipe and outer coil. In this regard, the outer pipe may be configured to rotatably support the jaws and the outer coil surrounding the flexible tool. Further, a proximal end of the outer pipe may be connected to a distal end of the outer coil.

In yet another non-limiting feature of the present invention, when the outer pipe moves forward the jaws may be rotated towards a closed position. Conversely, when the outer pipe moves rearward the jaws may be rotated towards an opened position.

Further, a projection may be provided at a proximal end of the jaws and a receiving aperture provided at a distal end of a distal-most rail. In this regard, the projection may be received within the receiving aperture such that the jaws are pivotably to the distal-most rail.

Additionally, the flexible tool may be detachably connectable to the proximal end of the shaft. Further, the shaft may include an outer pipe and outer coil. For example, the outer pipe may be configured to rotatably support the jaws and the outer coil may provide a covering for the flexible tool.

Additionally, rotation of at least one of the outer coil, flexible wire and a sheath, press-fitted to a rear end of the flexible tool, is configured to rotate the flexible tool.

In another non-limiting aspect of the present invention, the clip applier may be part of clip applier apparatus. In this regard, the clip applier apparatus may include at least one surgical clip; a shaft having a proximal end and a distal end, the distal end of the shaft comprising a flexible tool having at least two rails connected to each other by at least one jointed connection, and the at least two rails configured to rotate about the jointed connection. Further, a pair of jaws may be provided at a distal end of the flexible tool, and an actuator may be provided at the proximal end of the shaft. In this regard, the actuator may be configured to advance the at least one surgical clip within the flexible tool.

Additionally, in another non-limiting feature of the present disclosure, a method of using a clip applier to apply a clip to a target area may be employed. In this regard, the clip applier may include a shaft with a proximal end and a distal end, the distal end of the shaft may have a flexible tool having at least two rails connected to each other by at least one jointed connection, and the at least two rails may be configured to rotate about the jointed connection. Further, the clip applier may also have a pair of jaws at a distal end of the flexible tool. Additionally, the clip applier may include an actuator. In this regard, the method of applying a clip to the target area may include flexing the flexible tool; and actuating the actuator such that a clip is advanced within the flexible tool.

In another non-limiting aspect of the present invention, the clip applier may be part of a surgical assembly. In this regard, the surgical assembly may include an endoscope having an elongated channel, and a shaft having a proximal end and a distal end, the distal end of the shaft comprising a flexible tool having at least two rails which are connected to each other by at least one jointed connection. Further, the at least two rails may be configured to pivot about the jointed connection, and at least the flexible tool may be configured to be inserted within the channel of the endoscope. Additionally, a pair jaws may be provided at a distal end of the flexible tool and an actuator may be provided at the proximal end of the shaft. In this regard, the actuator may be configured to advance a surgical clip within the flexible tool.

BRIEF DESCRIPTION OF THE DRAWINGS

The present invention is further described in the detail description which follows, in reference to the noted plurality of drawings, by way of non-limiting examples of preferred embodiments of the present invention, in which like characters represent like elements throughout the several views of the drawings, and wherein:

FIGS. 1A and 1B, FIG. 1A is a perspective view of a clip applier according to a non-limiting embodiment of the present invention.

DETAILED DESCRIPTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1A:
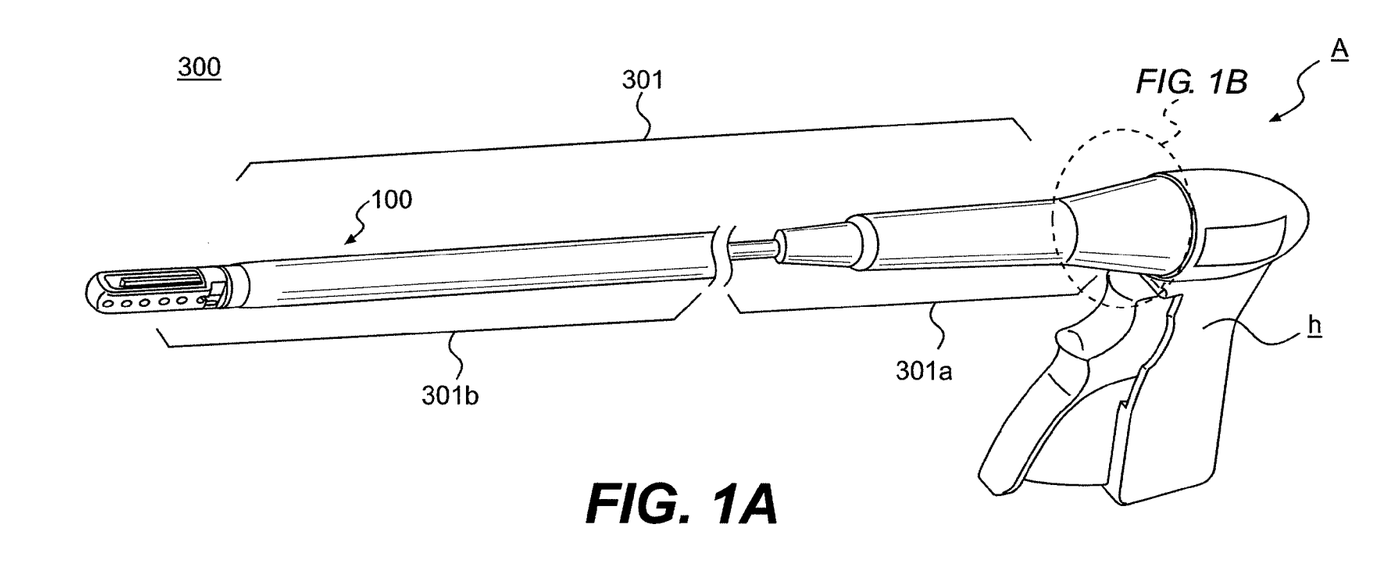
Figure 1B:
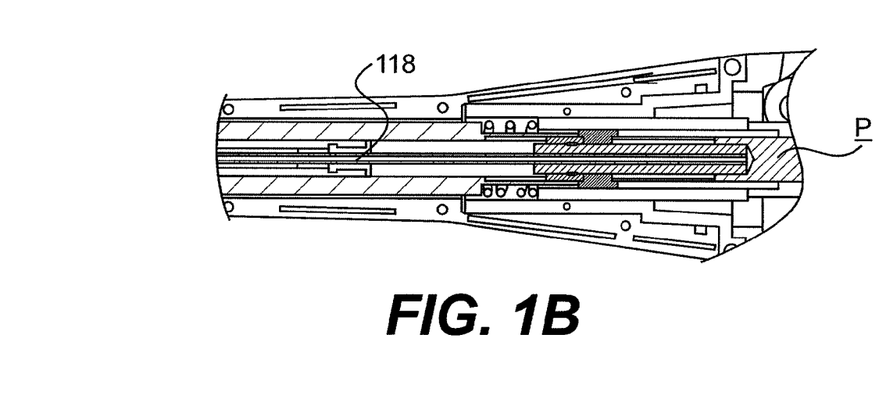
FIG. 1B is an enlarged section view.
Figure 3:
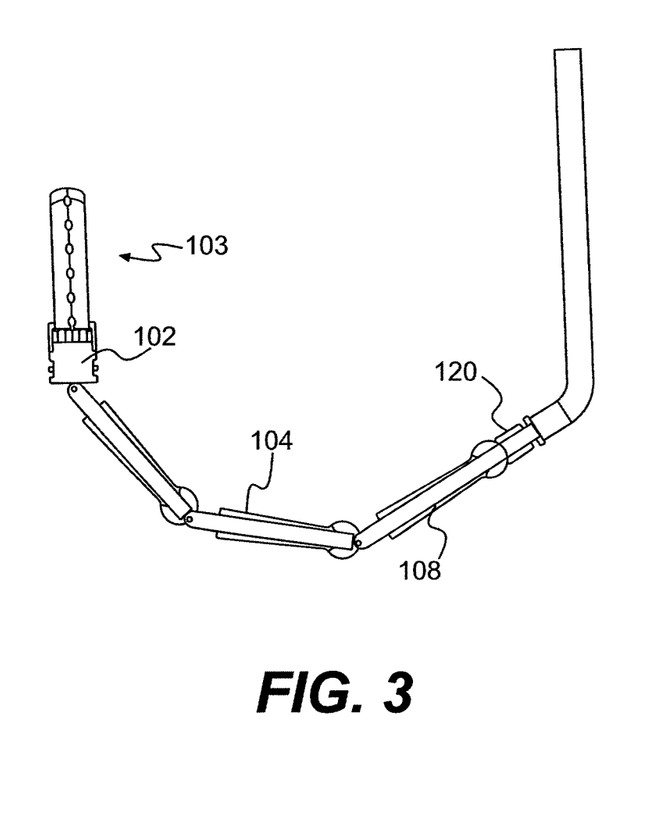
FIG. 3 is a side view of the flexible tool illustrating rails of the flexible tool articulated at connection points.

Referring to the drawings, FIG. 1 shows a flexible tool 100 of a clip applier 300 for applying a surgical clip (104, as shown in, e.g., FIG. 3) to a target area during a surgical procedure. In this regard, the clip applier 300 may include a shaft 301 having a proximal end 301a and a distal end 301b. Further, the distal end 301b of the shaft 301 may include the flexible tool 100. The flexible tool 100 may have at least two rails 108 connected to each other by at least one jointed connection 106 such that the rails 108 are configured to rotate about the jointed connection 106. Further, each rail segment may have both an upper side edge 108U and a lower side edge 108L extending in a longitudinal direction of the shaft 301, and wherein opposing rails segments 108 are not connected to each other at the upper side edges 108U and the lower side edges 108L.

Additionally, as shown in FIGS. 2, 3, 4A and 4B, jaws 103 are provided at a distal end of the flexible tool 100. Further, as shown in FIG. 1, an actuator A may be provided at a proximal end 301a of the shaft 301. In this regard, the actuator A may be configured to open and close the jaws 103 (e.g., either directly or through a mechanism which couples an action of the actuator to movement of the jaws) and advance the surgical clip 104 within the flexible tool 100.

Figure 5A:
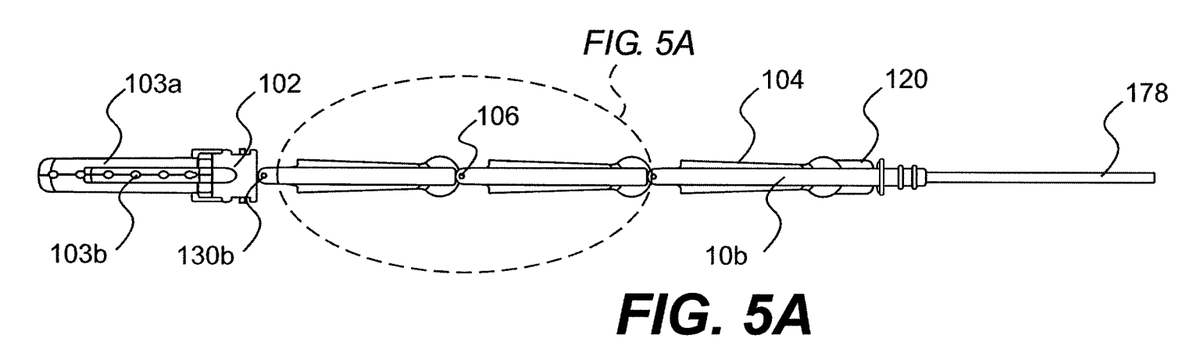
FIG. 5A is a detailed view of surgical clips positioned within the rails of the flexible tool.
Figure 5B:
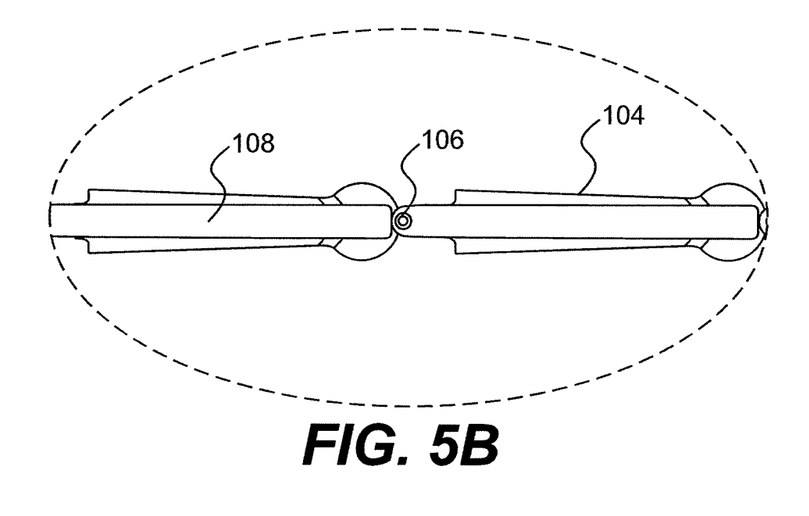
FIG. 5B is an exploded view showing the surgical clip, connection point and rails in further detail.

FIGS. 5A and 5B shows the flexible tool 100 having the plurality of rails 108 and the jointed connection 106 comprising a plurality of jointed connections (also 106). Therefore, it should be appreciated that the plurality of rails 108 may be provided in any number suitable for achieving a desired flexibility of the flexible tool 100. Additionally, the rails 108 (as well as surgical clips which are configured to be received therein) may also be of a length suitable to achieve the desired flexibility of the flexible tool 100.

In other words, the larger the number of rails 108, the more flexible the flexible tool 100 becomes. Similarly, the shorter the length of the rails 108, the more flexible the flexible tool 100 becomes. Referring again to FIGS. 5A and 5B, the jointed connection 106 may comprise any suitable connector which would allow the rails 108 to rotate about the connection 106; thereby further providing the flexible tool 100 with the desired flexibility. In other words, the plurality of rails 108 and jointed connections 106 are configured to allow the distal end 301b of the shaft to bend at various locations. In this regard, the jointed connection 106 may comprise a pin (also 106), a flexible material connecting adjacent rails, or a male/female connection.

However, one of ordinary skill in the art would recognize that other suitable connectors capable of providing flexibility to the tool may be employed without departing from the spirit and scope of the present invention.

Figure 8:
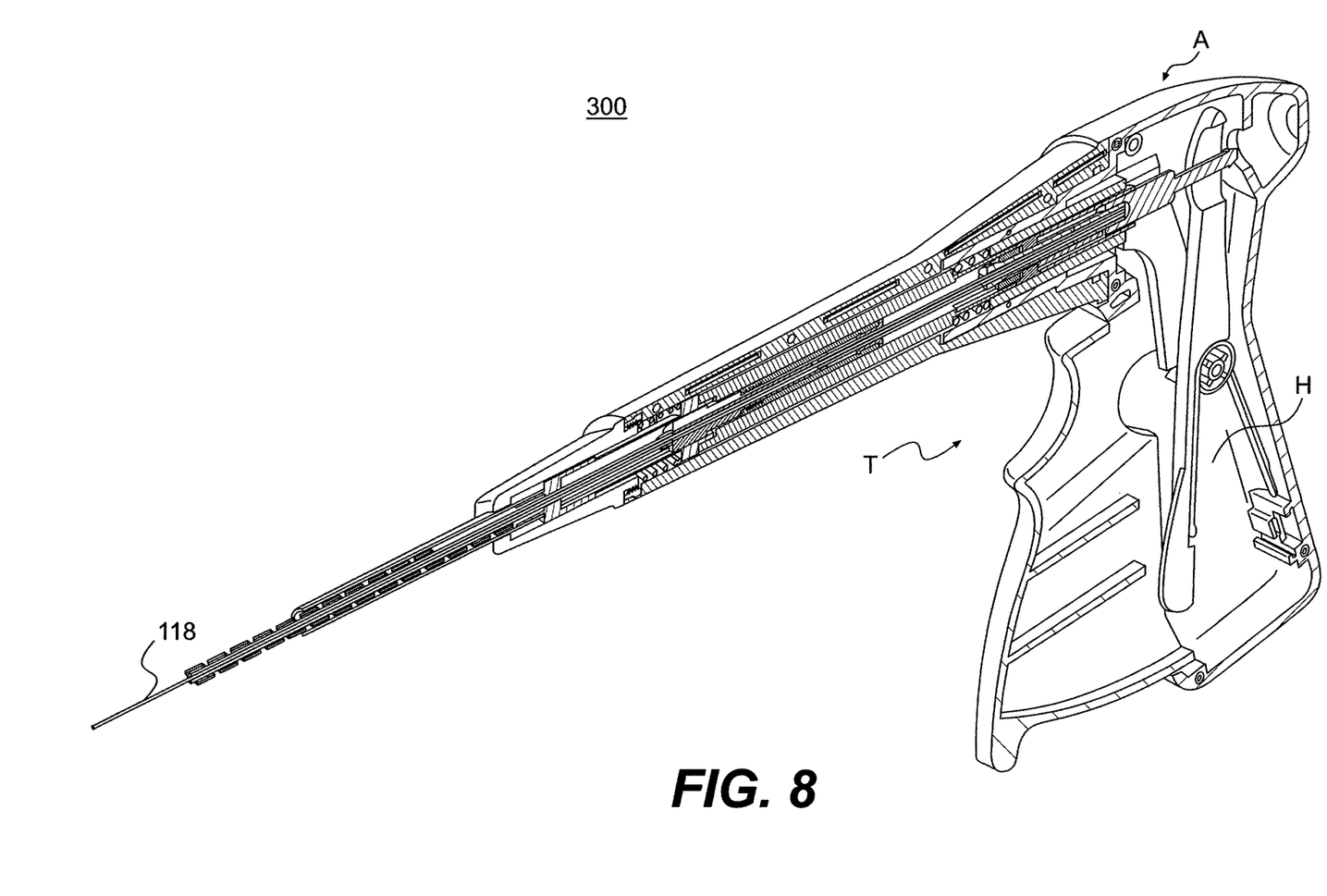
FIG. 8 is a cross-sectional view of a hand-piece of the clip applier.

Referring to FIG. 8, the flexible tool 100 (as shown in FIG. 1) may be coupled to an actuator A comprising a hand-piece H having a trigger T for actuating a flexible wire 118 in a forward direction (i.e., towards a distal end of the clip applier). In this regard, the actuator A may also include a flexible wire 118 connected to a pusher 120 and coupled to the hand-piece H. Therefore, both the flexible wire 118 and pusher 120 may be actuateable towards in a forward direction upon actuation of the handpiece H. Further, upon actuation, the pusher 120 may be configured to engage a rear surface of a proximal-most surgical clip 104 so as to advance the surgical clip(s) 104 within the flexible tool 100 and in the forward direction towards the jaws 103.

According to another feature, as shown in FIG. 8, the flexible wire may be connected to a suitable actuating mechanism, e.g. (a piston), which is configured to reciprocate linearly in a backwards and forward (i.e., proximal and distal) direction. In this regard, depression of a trigger T provided on the hand piece H may cause the piston P to be actuated linearly in a forward direction, thereby causing the flexible wire 118 and pusher 120 to be actuateable in the forward direction. More simply put, upon actuation of the piston P, the pusher 120 may be configured to engage a rear surface of a proximal-most surgical clip 104 so as to advance the surgical clip 104 within the flexible tool 100 and towards the jaw members 103a, 103b.

However, one of ordinary skill in the art would recognize that other suitable actuators capable of advancing the surgical clips with the flexible tool may be employed without departing from the spirit and scope of the present invention.

Figure 4A:
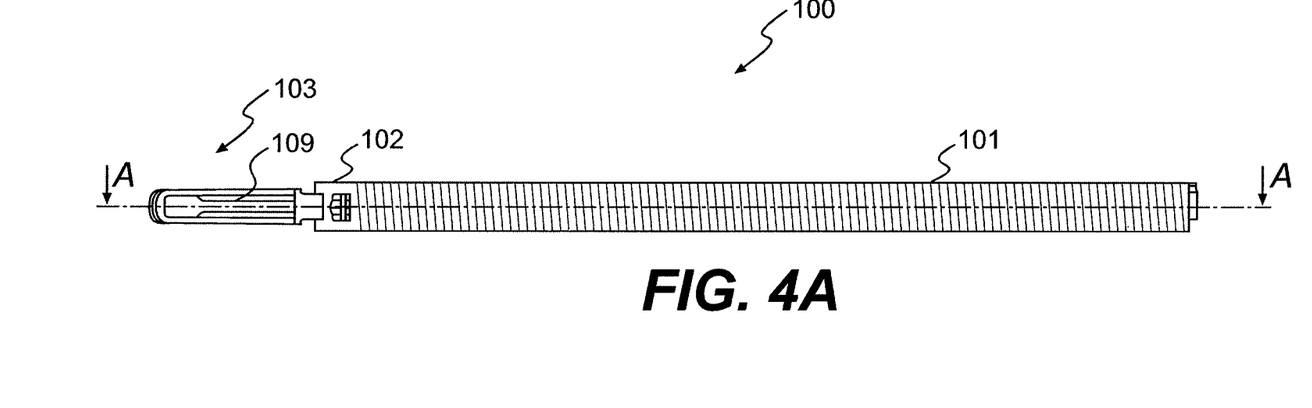
FIG. 4A is a top plan view of the flexible tool.
Figure 4B:
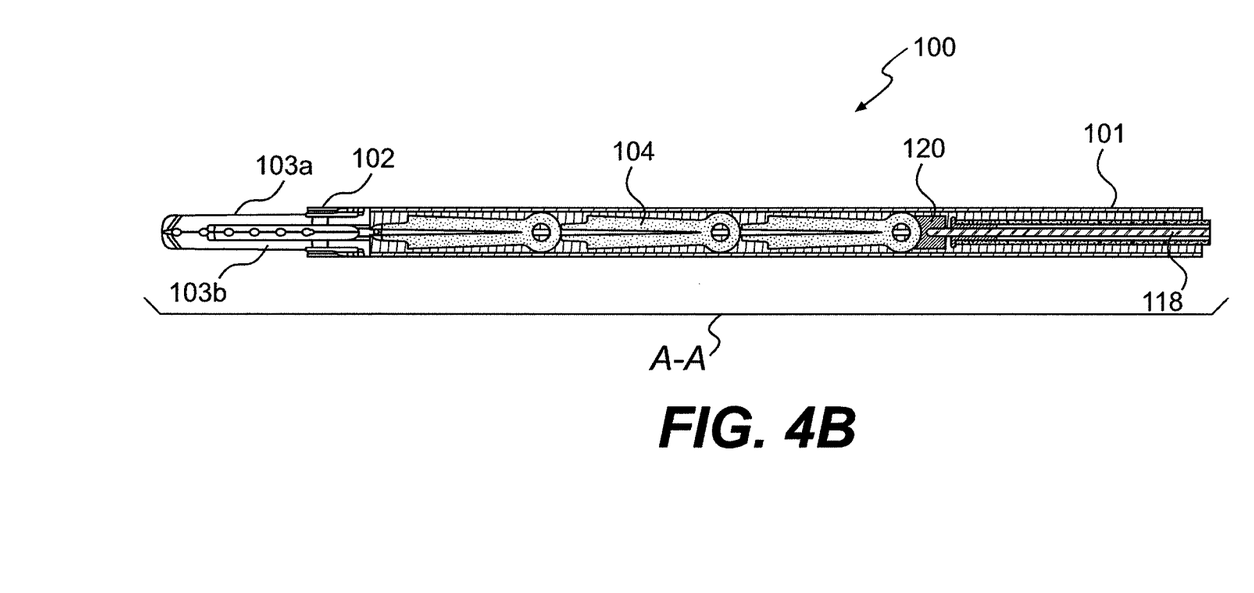
FIG. 4B is a cross-sectional view of the flexible tool of FIG. 4 taken along section A—A of FIG. 4A.

Additionally, as shown in FIGS. 4A and 4B, the flexible tool 100 may include an outer pipe 102 and an outer coil 101. In this regard, the outer pipe 102 may be configured to rotatably support the jaw members 103a, 103b and the outer coil 101 may provide an outer resilient covering of the flexible tool 100. In this regard, a proximal end of the outer pipe 102 may be connected to a distal end of the outer coil 101 by any suitable connection (e.g., by welding or adhesive). As illustrated in FIGS. 6A-6F, the outer pipe 102 may move in the forward direction so that the jaw members 103a, 103b rotate to a closed position (see FIGS. 6A and 6B), and the outer pipe 102 may move in the rearward direction so that the jaw members 103a, 103b rotate towards an opened position (see FIGS. 6C and 6D).

Additionally, as shown in FIGS. 6A-6D, the outer pipe 102 may be configured to rotatably support the jaw members 103a, 103b and the outer coil 101 may comprise the outer covering of the flexible tool 100.

Figure 6A:
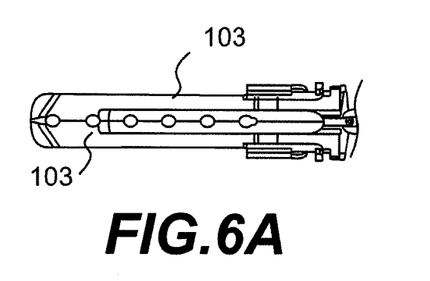
FIGS. 6A-6F are perspective views of various opened and closed positions of jaws of the flexible tool of the present invention.
Figure 6B:
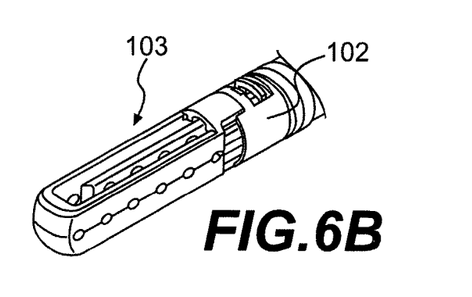
Figure 6C:
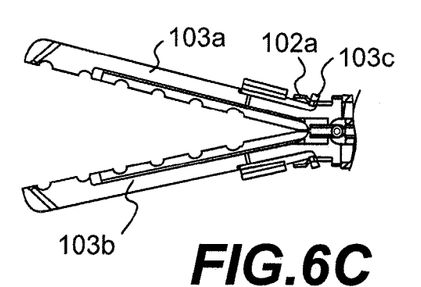
Figure 6D:
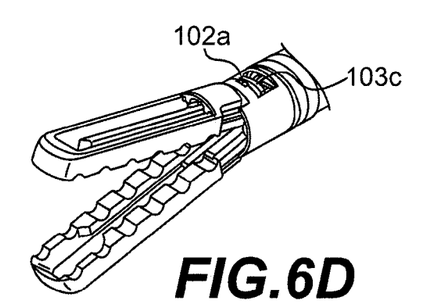
Figure 6E:
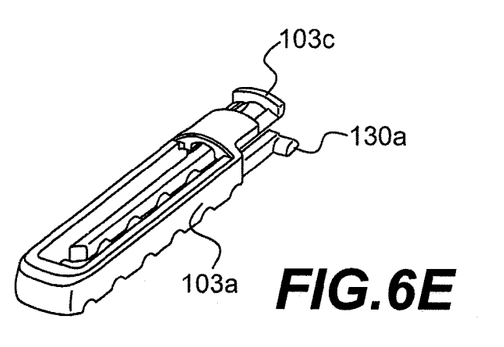

Additionally, as shown in FIG. 6E, a projection 130a may be provided at a proximal end of the jaws 103 and a receiving aperture provided at a distal end of a distal-most rail 108. In this regard, the projection 130a may be received within the receiving aperture 130b (as shown in FIG. 5A) thereby rotatably coupling the jaw members 103a to the distal-most rail 108.

Figure 6F:
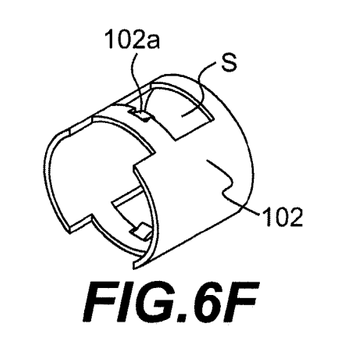

According to another feature of the present invention, as shown in FIG. 6F, since a rear end 103c of the jaws 103 (e.g., comprising a protrusion) may be inserted into a receiving aperture S (or slit) of the outer pipe, the jaws 103 may be configured to rotate as the outer pipe 102 reciprocates. In this regard, the outer pipe protrusion 102a proximate the rear ends of the jaws 103 may engage the rear end of jaws 103; thereby, causing the jaw members 103a, 103b to rotate.

Figure 2:
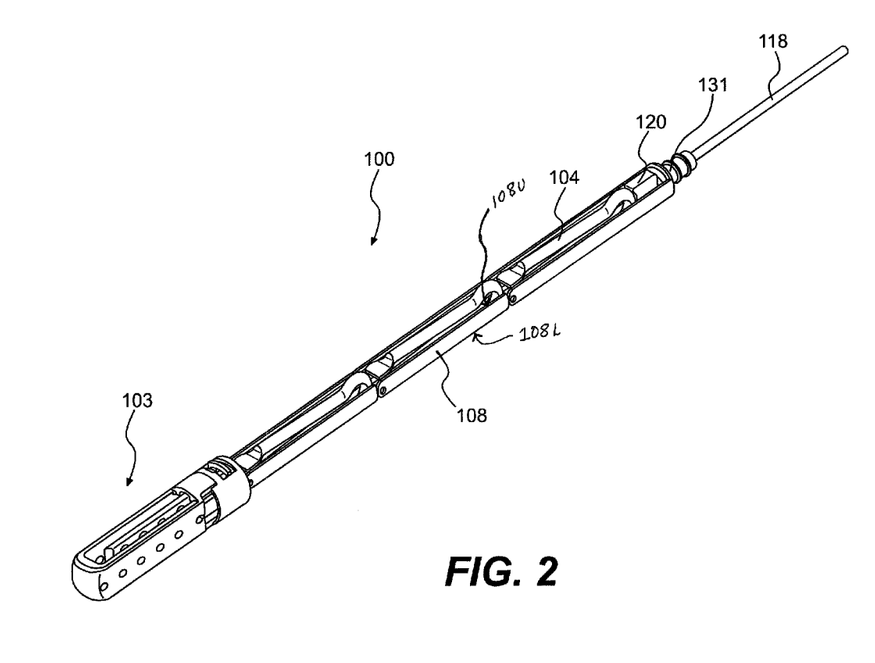
FIG. 2 is a perspective view of a flexible tool of the clip applier according to a non-limiting embodiment of the present invention.

Additionally, as illustrated in FIG. 2, the pusher 120 may be positioned between the rails 108. In this regard, the pusher 120 may be rotated about a longitudinal axis of the shaft 301 by rotating the flexible wire 118 connected to the pusher 120. Further, since a sheath 131 may be press-fitted (or otherwise fitted) to the rear end of the proximal-most rail 108, the sheath 131 may rotate concurrently with the rails 108. Further, since the pusher 120, the flexible wire 118, and the rails 108 are all coupled to each other, the flexible tool 100 may be rotated by rotating the outer coil 100, the flexible wire 118 and/or the sheath 131.

Further, as illustrated in FIGS. 2 and 5B, a length of the surgical clip 104 may be approximately the same as a length of the rails 108. According to another feature, and as shown in FIG. 7D each jaw may comprise an inwardly projecting ledge 109. In this regard, the ledge 109 may be configured to project inwardly from an inner surface of a corresponding jaw member 103a, 103b so as to engage the surgical clip 104 and temporarily expand the surgical clip 104 from a pre-biased closed position to an open position in order to clamp the target area (see, FIGS. 7A-7E).

In more exemplary detail, the jaws 103 may be actuated so as to clamp a target area TA therebetween. Subsequent to clamping the target area TA, the distal-most surgical clip 104 may be advanced such that a front end thereof engages the projecting ledge 109 (e.g., as the front end of the surgical clip 104 is advanced along the projecting ledges), thereby expanding the surgical clip 104 to an opened position from the pre-biased closed position. Further, the surgical clip 104 may return to the pre-biased closed position after the surgical clip 104 advances pass a point where the projecting ledge 109 terminates; whereupon the surgical clip 104 is allowed to return to a pre-biased closed position and clamp the target area TA therebetween. Further, the jaws 103 may be actuated to an opened position so as to release the target area TA, while the surgical clip 104 continues to clamp target area TA.

Now referring to FIGS. 1 and 2, the flexible tool 100 may be detachably coupled to the proximal end of the shaft 301a.

Referring to FIGS. 2 and 4a, at least one of the outer coil 101, flexible wire 118 and a sheath 131, press-fitted to a rear end of the flexible tool 100, may be configured to rotate the flexible tool 100.

Figure 7A:
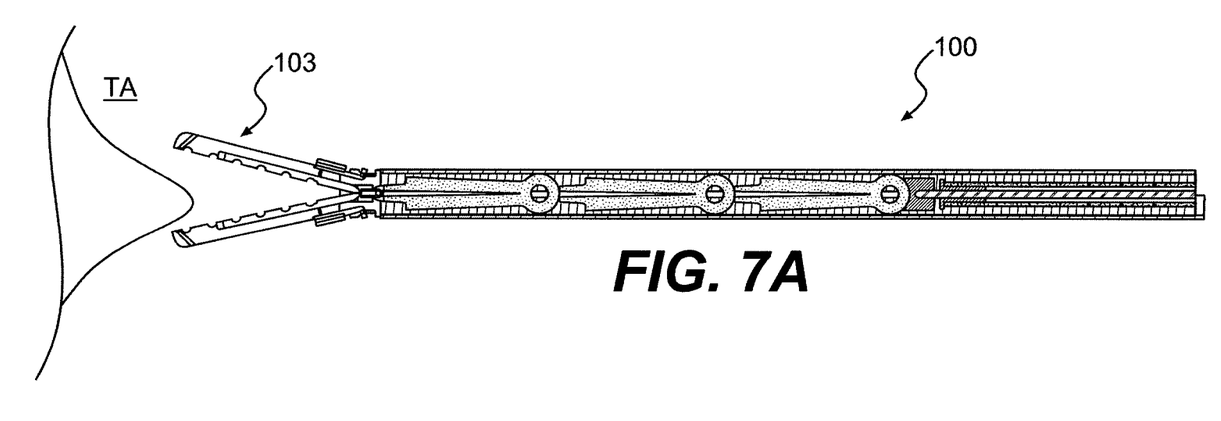
FIGS. 7A-7E illustrate the flexible tool performing a surgical procedure for clamping a target area.
Figure 7B:
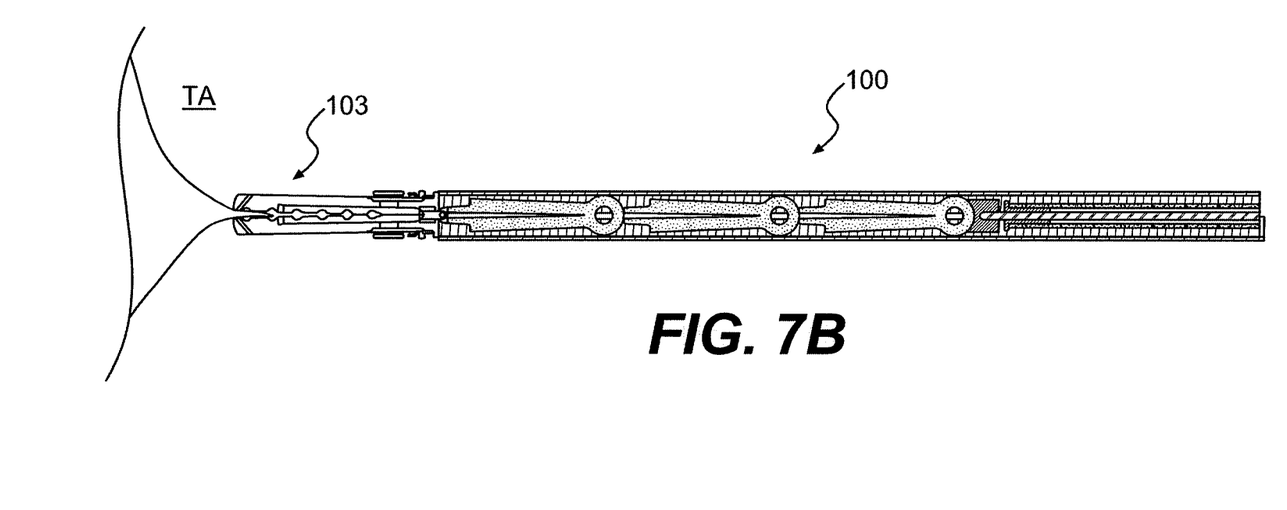
Figure 7C:
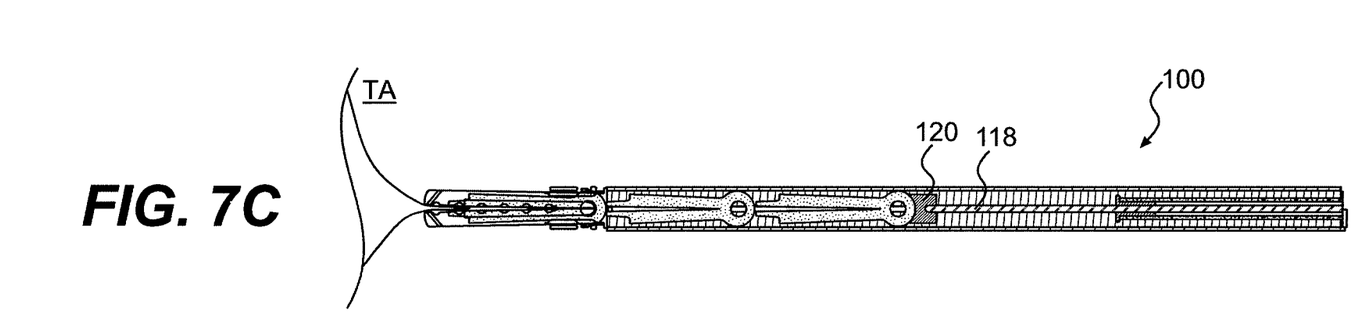
Figure 7D:
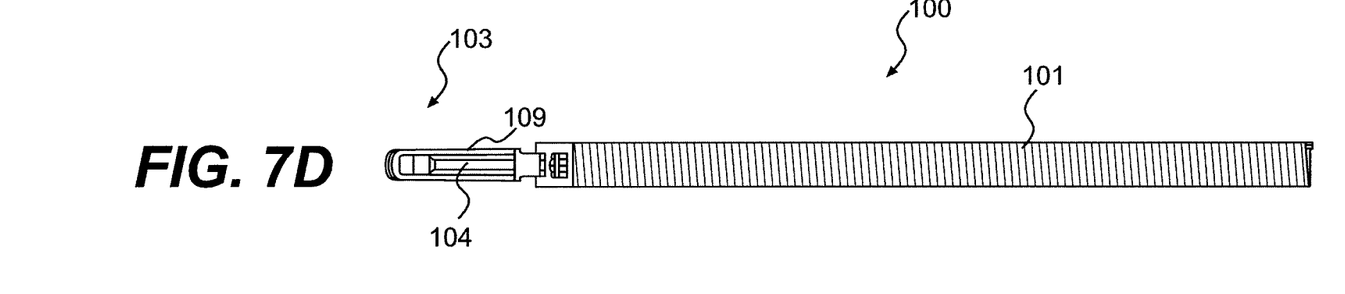

With reference to FIGS. 7A-7E, operation of the clip applier is explained in further detail. Referring now to FIG. 7A, when no force is exerted on the clip 104, the clip is in a closed position because the clip 104 is pre-biased towards a closed position, much like a bobby pin. Therefore, when the clip 104 engages the rails 109 of the jaws 103 the clip 104 is urged to open so as to prepare to, e.g., engage, receive or clamp tissue positioned between the jaws (see FIG. 7C).

Figure 7E:
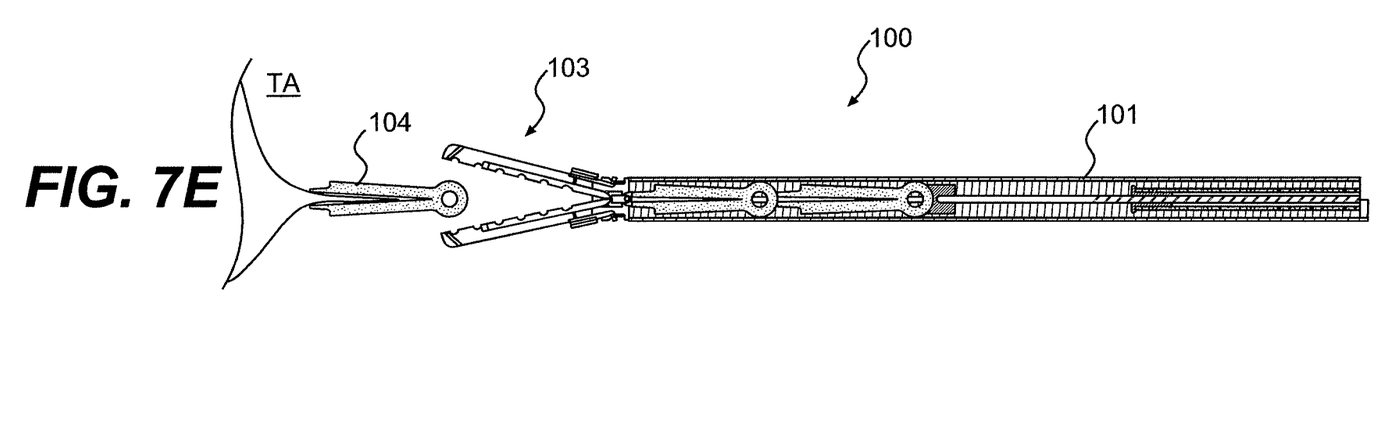

In this regard, as discussed supra, when the clip 104 is advanced forward to a portion of the jaws 103 which does not include the inwardly projecting ledge 109 (e.g., a position where the inwardly projecting ledge 109 terminates), the surgical clip 104 disengages the ledge 109, and, as a result, the surgical clip 104 is allowed to return to its pre-biased closed position; thereby clamping the tissue held between the jaws (see FIG. 7E).

In this regard, the jaws 103 may be configured to pivot about a support to opened and closed positions. For example, as shown in FIG. 7B the jaws 103 may pivot in the closing direction when the outer pipe 102 moves forward and comes in contact with the jaws 103. Further, when the outer pipe 102 moves in the rearward (or proximal) direction (i.e., opposing the forward, or distal, direction) the jaws may be opened (see FIG. 7E). In this regard, the outer pipe 102 may be provided with the outer pipe protrusion 102a which is configured to engage at least one of the jaw members 103a or 103b. For example, the outer pipe protrusion 102a may come into contact with a proximal end portion of at least one of the jaws 103 (see FIG. 6D), thereby pivoting the jaw members 103a, 103b to an open position. Additionally, a front end of the outer pipe 102, when actuated in a forward direction, may engage surfaces of the jaws 103 in order to rotate the jaws to a closed position (see FIG. 6A).

More simply put, the outer pipe 102 may be provided with cam surfaces which engage the jaw members 103a, 103b in order to open and close the jaws 103.

However, one of ordinary skill in the art would recognize that other suitable mechanisms for opening and closing the jaws may be employed without departing from the spirit and scope of the present invention.

FIGS. 7A-7E show a procedure for clamping a target area TA. For example, the surgical clip applier 300 may approach a target area TA and clamp the target area TA by moving the outer coil 101 and outer pipe 102 forward, thereby closing the jaw members 103a, 103b. Subsequently, the pusher 120 may be actuated in the forward direction in order to advance the surgical clip 104 within the flexible tool 100. For example, at this point, the surgical clip 104 may be advanced forward to a portion of the jaws 103 which does not include the jaw rails (see FIG. 7D). In this regard, the surgical clip 104 may then disengage the jaw rail 109, and clamp the target area TA held by the jaw members 103a, 103b, since the surgical clip 104 is pre-biased towards its closed position.

Further, when the jaw members 103a, 103b are opened after deployment of the surgical clip 104, the clip applier 103 can be removed from the target area TA, leaving the surgical clip 104 in place (FIG. 7E).

Additionally, the present invention allows for the clip applier 300 to have a diameter of about 3 mm to 5 mm and a length of about 1 to 2 meters, i.e., in order to provide a flexible minimally-invasive clip applier, although those of skill in the art would appreciate that the clip applier would have other suitable diameters and lengths. As discussed in further detail below, the flexible clip applier 300 can be inserted into the channel 400a of an endoscope 400 (see FIG. 9) and the flexible tool 100 may include a small cartridge, for example, having three surgical clips (see FIG. 10); although any suitable desirable number of surgical clips may be provided within the cartridge. In this regard, due to the size and dimension of the flexible tool 100, the flexible tool (as well as the surgical clip cartridge) may be provided to be detachable and disposable (e.g., as shown in FIG. 2).

Figure 9:
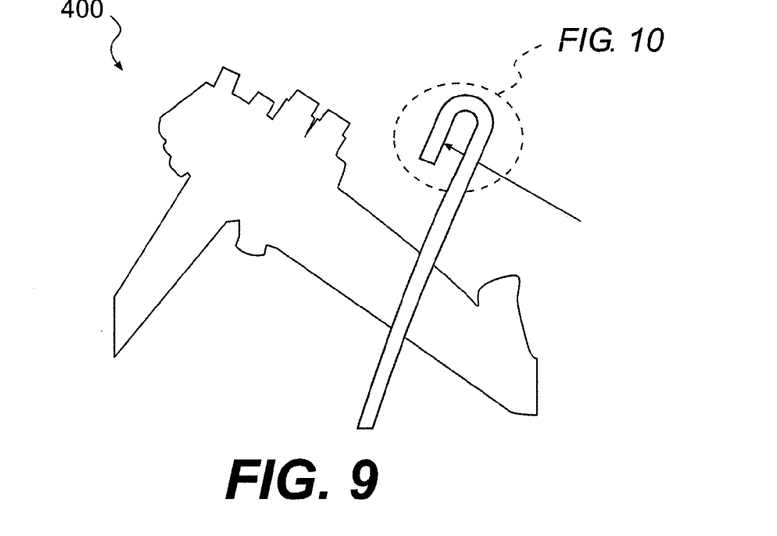
FIG. 9 is a perspective view of an endoscope for performing a minimally invasive surgical procedure.
Figure 10:
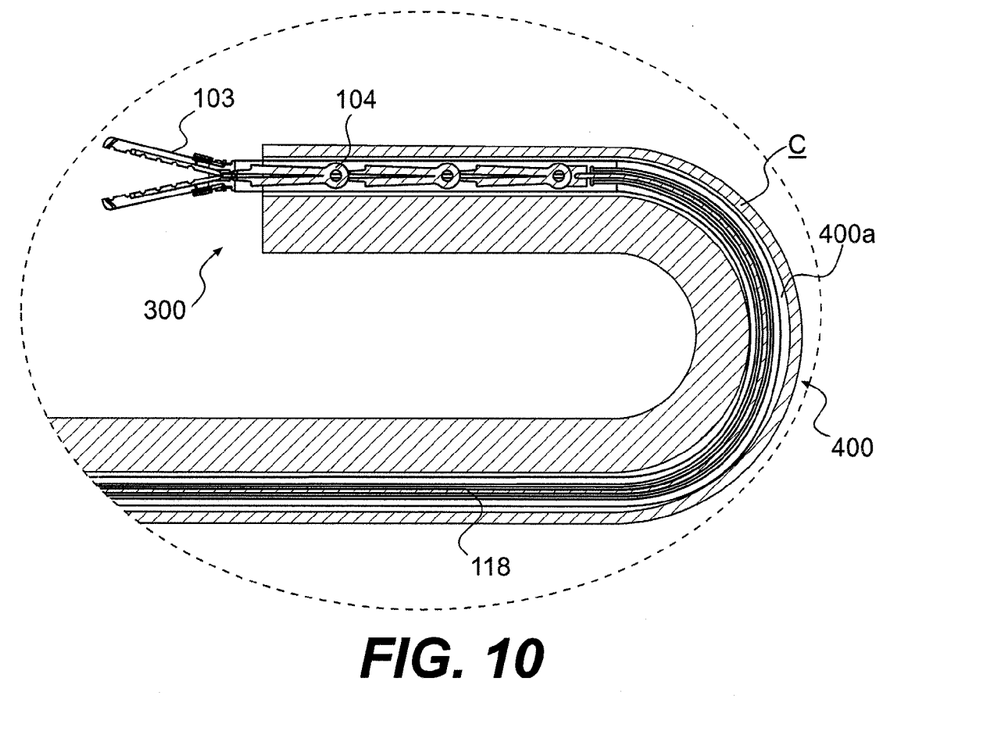
FIG. 10 is a cross-sectional view of the clip applier of the present invention inserted within an elongated channel of the endoscope.

Further, it should also be appreciated that the clip applier 300 of the present invention can be used as part of a surgical assembly (see FIGS. 9 and 10). For example, FIG. 10 illustrates a surgical assembly including an endoscope 400 having an elongated channel 400a, at least one surgical clip 104, and a clip applier 300. In this regard, as discussed above, the clip applier 300 may include a shaft 301 having a proximal end 301a and a distal end 301b. The distal end 301b of the shaft 301 may include a flexible tool 100 having at least two rails 108 which are connected to each other by at least one jointed connection 106. Similar to the description above, the rails 108 may be configured to rotate about the jointed connection 106 and the flexible tool 100 may be configured to be inserted within the channel 400a of the endoscope 400. Additionally, the jaws 103 may be provided at a distal end of the flexible tool 100, and an actuator A (e.g., a hand piece or any other suitable actuating mechanism) provided at the proximal end 301a of the shaft 301, the actuator A configured to advance the surgical clip 104 within the flexible tool 100. Additionally, the flexible tool 100 may be configured to extend pass a longitudinally curved region C of the channel 400a of the endoscope 400, e.g., as illustrated in FIG. 10.

5941 It is further noted that the foregoing examples have been provided merely for the purpose of explanation and are in no way to be construed as limiting of the present invention. While the present invention has been described with reference to a preferred embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A clip applier assembly for applying a surgical clip to a target area during a surgical procedure, the clip applier comprising:
at least one surgical clip;
a shaft having a proximal end and a distal end, the distal end of the shaft comprising a flexible tool having at least two rails connected to each other by at least one jointed connection, the at least two rails configured to rotate about the jointed connection, each of the rails comprising a pair of opposing rail segments which are spaced apart in a diametrical direction of the flexible tool so as to define a corresponding space between each of the pair of opposing rail segments, the shaft further comprises an outer pipe and an outer coil, the outer pipe being configured to rotatably support a pair of jaws provided at a distal end of the flexible tool and the outer coil surrounding the flexible tool,
wherein the at least one surgical clip is received within the corresponding space, and a length of the surgical clip is approximately the same as a length of the rails,
wherein rear ends of at least one of the pair of opposing rail segments are pivotably connected to front ends of at least another of the pair of opposing rail segments to define the jointed connection,
each rail segment having both an upper side edge and a lower side edge extending in a longitudinal direction of the shaft, wherein opposing rail segments are spaced apart from each other at the upper side edges and the lower side edges, and wherein the jointed connection allows pivoting of the opposing rail segments in a direction extending from the upper side edges to the lower side edges;
an actuator provided at the proximal end of the shaft, the actuator configured to advance the surgical clip within the flexible tool;
a projection provided at a proximal end of each of the jaws, and each of jaws being provided with a rear end protrusion; and
receiving apertures provided at a distal end of a distal-most rail, wherein each of the projections is received within a corresponding one of the receiving apertures such that the jaws are pivotably coupled to the distal-most rail, and wherein each of the rear end protrusions is inserted into a corresponding receiving aperture of the outer pipe.

2. The clip applier assembly according to claim 1, wherein the at least two rails comprises at least three rails, and wherein the at least one jointed connection comprises a plurality of jointed connections such that a jointed connection of the plurality of jointed connections connects the at least two rails of the at least three rails.

3. The clip applier assembly according to claim 1, wherein the jointed connection comprises a pin.

4. The clip applier assembly according to claim 1, wherein the actuator further comprises a hand-piece.

5. The clip applier assembly according to claim 4, wherein the actuator further comprises a flexible wire connected to a pusher and coupled to the hand-piece, both the flexible wire and pusher being actuateable towards the distal end of the shaft such that, upon actuation of the handpiece, the pusher engages a proximal surface of a proximal-most surgical clip so as to advance the surgical clip within the flexible tool and towards the jaws.

6. The clip applier assembly according to claim 5, wherein the shaft further comprises an outer pipe and outer coil, the outer pipe being configured to rotatably support the pair of jaws and the outer coil surrounding the flexible tool.

7. The clip applier assembly according to claim 6, wherein rotation of at least one of the outer coil, flexible wire and a sheath, press-fitted to a rear end of the flexible tool, is configured to rotate the flexible tool.

8. The clip applier assembly according to claim 1, wherein the jaws comprise an inwardly projecting ledge, the ledge being configured to engage the surgical clip and temporarily expand the surgical clip from a pre-biased closed position to an open position so as to engage the target.

9. The clip applier assembly according to claim 1, wherein the at least two rails and the jointed connection are configured together to allow the distal end of the shaft to bend at a plurality of locations.

10. The clip applier assembly according to claim 1, wherein a proximal end of the outer pipe is connected to a distal end of the outer coil.

11. The clip applier assembly according to claim 1, wherein when the outer pipe moves forward the jaws rotate towards a closed position, and when the outer pipe moves rearward the jaws rotate towards an opened position.

12. The clip applier assembly according to claim 1, wherein the flexible tool is detachably connectable to the proximal end of the shaft.

13. A surgical assembly, comprising:
  at least one surgical clip;
  an endoscope having an elongated channel;
  a shaft having a proximal end and a distal end, the distal end of the shaft comprising a flexible tool having at least two rails which are connected to each other by at least one jointed connection, the at least two rails configured to pivot about the jointed connection, each of the rails comprising a pair of opposing rail segments which are spaced apart in a diametrical direction of the flexible tool so as to define a corresponding space between each of the pair of opposing rail segments, the shaft further comprises an outer pipe and an outer coil, the outer pipe being configured to rotatably support a pair of jaws provided at a distal end of the flexible tool and the outer coil surrounding the flexible tool,
  wherein the at least one surgical clip is received within the corresponding space, and a length of the surgical clip is approximately the same as a length of the rails, and
  wherein rear ends of at least one of the pair of opposing rail segments are pivotably connected to front ends of at least another of the pair of opposing rail segments to define the jointed connection, each rail segment having both an upper side edge and a lower side edge extending in a longitudinal direction of the shaft, wherein opposing rail segments are spaced apart from each other at the upper side edges and the lower side edges, and wherein the jointed connection allows pivoting of the opposing rail segments in a direction extending from the upper side edges to the lower side edges,
  wherein at least the flexible tool is configured to be inserted within the channel of the endoscope;
  an actuator provided at the proximal end of the shaft, the actuator configured to advance the surgical clip within the flexible tool;
  a projection provided at a proximal end of each of the jaws, and each of jaws being provided with a rear end protrusion; and
  receiving apertures provided at a distal end of a distal-most rail, wherein each of the projections is received within a corresponding one of the receiving apertures such that the jaws are pivotably coupled to the distal-most rail, and wherein each of the rear end protrusions is inserted into a corresponding receiving aperture of the outer pipe.

14. The surgical assembly according to claim 13, wherein the flexible tool is configured to extend past a curved longitudinal region of the channel of the endoscope.

15. The clip applier according to claim 13, wherein the jointed connection comprises a pin.

16. The clip applier according to claim 13, wherein the actuator further comprises a hand-piece.

17. A method of using a clip applier to apply a clip to a target area, the clip applier having a shaft with a proximal end and a distal end, the distal end of the shaft having a flexible tool having at least two rails connected to each other by at least one jointed connection, and the at least two rails configured to rotate about the jointed connection, each of the rails comprising a pair of opposing rail segments which are spaced apart in a diametrical direction of the flexible tool so as to define a corresponding space between each of the pair of opposing rail segments, wherein the clip is received within the corresponding and the length of the clip is approximately the same as a length of the rails, wherein rear ends of at least one of the pair of opposing rail segments are pivotably connected to front ends of at least another of the pair of opposing rail segments to define the jointed connection, and the shaft further comprises an outer pipe and an outer coil, the outer pipe being configured to rotatably support a pair of jaws provided at a distal end of the flexible tool and the outer coil surrounding the flexible tool,
  the clip applier further having an actuator, the method comprising:
  providing each rail segment having both an upper side edge and a lower side edge extending in a longitudinal direction of the shaft such that opposing rail segments are spaced apart from each other at the upper side edges and the lower side edges, and the jointed connection allowing pivoting of the opposing rail segments in a direction extending from the upper side edges to the lower side edges;
  flexing the flexible tool; and
  actuating the actuator such that the clip is advanced within the flexible tool;
  providing a projection at a proximal end of each of the jaws, and each of jaws being provided with a rear end protrusion; and
  receiving apertures provided at a distal end of a distal-most rail, wherein each of the projections is received within a corresponding one of the receiving apertures such that the jaws are pivotably coupled to the distal-most rail, and wherein each of the rear end protrusions is inserted into a corresponding receiving aperture of the outer pipe.

* * * * *